US006287566B1

(12) United States Patent
Dertzbaugh

(10) Patent No.: US 6,287,566 B1
(45) Date of Patent: Sep. 11, 2001

(54) **PROTECTIVE PEPTIDES NEUROTOXIN OF *C. BOTULINUM***

(75) Inventor: Mark T. Dertzbaugh, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 08/446,114

(22) Filed: May 19, 1995

(51) Int. Cl.[7] .......................... A61K 39/00; A61K 39/02; A61K 39/08
(52) U.S. Cl. ..................................... 424/190.1; 424/192.1; 424/239.1; 530/300; 530/350; 930/200
(58) Field of Search ............................... 424/236.1, 239.1, 424/247.1, 184.1, 185.1, 190.1, 192.1; 530/350, 300; 930/10, 200

(56) References Cited

U.S. PATENT DOCUMENTS 5,268,276 * 12/1993 Holmgren et al. .

FOREIGN PATENT DOCUMENTS

562132A1 * 9/1993 (EP) .
9107979 * 6/1991 (WO) .

OTHER PUBLICATIONS

Binz et al. (1990) J. Biol. Chem. 265(16), 9153–9158 "The Complete Sequence of Botulinum Neurotoxin type A and comparsion with other Clostrididl Neurotoxins".*
Lockman et al (1983) 258(22), 13722–13725 "Nucleotide sequence analysis of the A2 and B subunits of Vibrio cholera Electrotoxin".*
Dertzbaugh et al. (1993) 61(1), 45–55 "Comparative Effectiveness of cholera Toxin B subunit and alkaline phosphotase as carriers for oral vaccine".*

* cited by examiner

*Primary Examiner*—Patricia A. Duffy
(74) *Attorney, Agent, or Firm*—Elizabeth Arwine; John Francis Moran; Charles H. Harris

(57) ABSTRACT

Methods for developing vaccines to protect from neurotoxins of *C. botulinum* have been developed. Truncated BoNT/A proteins of about 15–30 kDa in size produced immune responses that provided protection from neuronal damage by *botulinum* neurotoxins.

5 Claims, No Drawings

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH: 40 base pairs
        (B) TYPE: nucleic acid
        (C) STRANDEDNESS: unknown
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: C. botulinum (xi) SEQUENCE DESCRIPTION: SEQ ID NO:1:

ATATGGAATT CGTTAATAAA CAATTTAATT ATAAAGATCC                      40

(2) INFORMATION FOR SEQ ID NO:2:

(i) SEQUENCE CHARACTERISTICS:
        (A) LENGTH: 42 base pairs
        (B) TYPE: nucleic acid
        (C) STRANDEDNESS: unknown
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: C. botulinum (xi) SEQUENCE DESCRIPTION: SEQ ID NO:2:

AGTATCGTCG ACTTTTAATT CTGTATCTAT TGTACTTCCA CC                   42

(2) INFORMATION FOR SEQ ID NO:3:

(i) SEQUENCE CHARACTERISTICS:
        (A) LENGTH: 32 base pairs
        (B) TYPE: nucleic acid
        (C) STRANDEDNESS: unknown
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: C. botulinum (xi) SEQUENCE DESCRIPTION: SEQ ID NO:3:

GATACAGAAT TCAAAGTTAT TGATACTAAT AG                                 32

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: unknown
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                 (A) ORGANISM: C. botulinum (xi) SEQUENCE DESCRIPTION: SEQ ID NO:4:

CTTTGCGTCG ACTCCCCCAA ATGTTCTAAG TTCC                                    34

(2) INFORMATION FOR SEQ ID NO:5:

(i) SEQUENCE CHARACTERISTICS:
                 (A) LENGTH: 39 base pairs
                 (B) TYPE: nucleic acid
                 (C) STRANDEDNESS: unknown
                 (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                 (A) ORGANISM: C. botulinum (xi) SEQUENCE DESCRIPTION: SEQ ID NO:5:

GGGTTAGAAT TCAGCTTTGA GGAACTTAGA ACATTTGGG                               39

(2) INFORMATION FOR SEQ ID NO:6:

(i) SEQUENCE CHARACTERISTICS:
                 (A) LENGTH: 45 base pairs
                 (B) TYPE: nucleic acid
                 (C) STRANDEDNESS: unknown
                 (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                 (A) ORGANISM: C. botulinum (xi) SEQUENCE DESCRIPTION: SEQ ID NO:6:

AGGACTGTCG ACCAAGTCCC AATTATTAAC TTTGATTGAT AAATC                        45

(2) INFORMATION FOR SEQ ID NO:7:

(i) SEQUENCE CHARACTERISTICS:
                 (A) LENGTH: 36 base pairs
                 (B) TYPE: nucleic acid
                 (C) STRANDEDNESS: unknown
                 (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                 (A) ORGANISM: C. botulinum (xi) SEQUENCE DESCRIPTION: SEQ ID NO:7:

TTAAATGAAT TCTCAATCAA AGTTAATAAT TGGGAC                                  36

(2) INFORMATION FOR SEQ ID NO:8:

(i) SEQUENCE CHARACTERISTICS:

(A) LENGTH: 33 base pairs
        (B) TYPE: nucleic acid
        (C) STRANDEDNESS: unknown
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: C. botulinum (xi) SEQUENCE DESCRIPTION: SEQ ID NO:8:

CTCTGGGTCG ACTTCTAACA GAATAACAGC TCC                33

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: unknown
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: C. botulinum (xi) SEQUENCE DESCRIPTION: SEQ ID NO:9:

GAAGTAAGAG CTCTGGATAA AATTGCGGAT ATAAC             35

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: unknown
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: C. botulinum (xi) SEQUENCE DESCRIPTION: SEQ ID NO:10:

GCTATGATTA ATATAAATAA ATTTTTGAAT CAATGC             36

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: unknown
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: C. botulinum (xi) SEQUENCE DESCRIPTION: SEQ ID NO:11:

TAACCGGTCG ACACCATAAG GGATCATAGA G                              31

(2) INFORMATION FOR SEQ ID NO:12:

(i) SEQUENCE CHARACTERISTICS:
          (A) LENGTH: 39 base pairs
          (B) TYPE: nucleic acid
          (C) STRANDEDNESS: unknown
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: C. botulinum (xi) SEQUENCE DESCRIPTION: SEQ ID NO:12:

AGTACTAAGC TTTTCATACA TACTATTATA TACAATAGC                      39

(2) INFORMATION FOR SEQ ID NO:13:

(i) SEQUENCE CHARACTERISTICS:
          (A) LENGTH: 35 base pairs
          (B) TYPE: nucleic acid
          (C) STRANDEDNESS: unknown
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: C. botulinum (xi) SEQUENCE DESCRIPTION: SEQ ID NO:13:

AAAAATAGAG CTCAATTATT TAATTTAGAA AGTAG                          35

(2) INFORMATION FOR SEQ ID NO:14:

(i) SEQUENCE CHARACTERISTICS:
          (A) LENGTH: 33 base pairs
          (B) TYPE: nucleic acid
          (C) STRANDEDNESS: unknown
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: C. botulinum (xi) SEQUENCE DESCRIPTION: SEQ ID NO:14:

ACCATCGTCG ACAAACATTA TATTATTACT AGC                            33

(2) INFORMATION FOR SEQ ID NO:15:

(i) SEQUENCE CHARACTERISTICS:
          (A) LENGTH: 37 base pairs
          (B) TYPE: nucleic acid
          (C) STRANDEDNESS: unknown
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: C. botulinum (xi) SEQUENCE DESCRIPTION: SEQ ID NO:15:

TATGGTGAAT TCATCTGGAC TTTACAGGAT ACTCAGG                                37

(2) INFORMATION FOR SEQ ID NO:16:

(i) SEQUENCE CHARACTERISTICS:
             (A) LENGTH: 27 base pairs
             (B) TYPE: nucleic acid
             (C) STRANDEDNESS: unknown
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: C. botulinum (xi) SEQUENCE DESCRIPTION: SEQ ID NO:16:

ATTTACGTCG ACATATTTAT TTGGATC                                           27

(2) INFORMATION FOR SEQ ID NO:17:

(i) SEQUENCE CHARACTERISTICS:
             (A) LENGTH: 31 base pairs
             (B) TYPE: nucleic acid
             (C) STRANDEDNESS: unknown
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: C. botulinum (xi) SEQUENCE DESCRIPTION: SEQ ID NO:17:

GATAAGGAAT TCAATGAAAA AGAAATCAAA G                                      31

(2) INFORMATION FOR SEQ ID NO:18:

(i) SEQUENCE CHARACTERISTICS:
             (A) LENGTH: 30 base pairs
             (B) TYPE: nucleic acid
             (C) STRANDEDNESS: unknown
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: C. botulinum (xi) SEQUENCE DESCRIPTION: SEQ ID NO:18:

CTTCATGTCG ACTACTTGAC TTAGATTTCC                                        30

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: unknown
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: C. botulinum (xi) SEQUENCE DESCRIPTION: SEQ ID NO:19:

```
AACATTGAAT TCAATTCAAG TTTGTATAGG GGG                                       33
```

(2) INFORMATION FOR SEQ ID NO:20:

(i) SEQUENCE CHARACTERISTICS:
        (A) LENGTH: 36 base pairs
        (B) TYPE: nucleic acid
        (C) STRANDEDNESS: unknown
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: C. botulinum (xi) SEQUENCE DESCRIPTION: SEQ ID NO:20:

```
TCCATCGTCG ACAGGAATAA ATTCCCATGA GCTACC                                   36
```

(2) INFORMATION FOR SEQ ID NO:21:

(i) SEQUENCE CHARACTERISTICS:
        (A) LENGTH: 207 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: C. botulinum (xi) SEQUENCE DESCRIPTION: SEQ ID NO:21:

```
Ile Lys Val Asn Asn Trp Asp Leu Phe Phe Ser Pro Ser Glu Asp Asn
1               5                   10                  15

Phe Thr Asn Asp Leu Asn Lys Gly Glu Glu Ile Thr Ser Asp Thr Asn
            20                  25                  30

Ile Glu Ala Ala Glu Glu Asn Ile Ser Leu Asp Leu Ile Gln Gln Tyr
        35                  40                  45

Tyr Leu Thr Phe Asn Phe Asp Asn Glu Pro Glu Asn Ile Ser Ile Glu
50                  55                  60
```

```
Asn Leu Ser Ser Asp Ile Ile Gly Gln Leu Glu Leu Met Pro Asn Ile
65                  70                  75                  80

Glu Arg Phe Pro Asn Gly Lys Lys Tyr Glu Leu Asp Lys Tyr Thr Met
                85                  90                  95

Phe His Tyr Leu Arg Ala Gln Glu Phe Glu His Gly Lys Ser Arg Ile
                100                 105                 110

Ala Leu Thr Asn Ser Val Asn Glu Ala Leu Leu Asn Pro Ser Arg Val
            115                 120                 125

Tyr Thr Phe Phe Ser Ser Asp Tyr Val Lys Lys Val Asn Lys Ala Thr
        130                 135                 140

Glu Ala Ala Met Phe Leu Gly Trp Val Glu Gln Leu Val Tyr Asp Phe
145                 150                 155                 160

Thr Asp Glu Thr Ser Glu Val Ser Thr Thr Asp Lys Ile Ala Asp Ile
                165                 170                 175

Thr Ile Ile Ile Pro Tyr Ile Gly Pro Ala Leu Asn Ile Gly Asn Met
            180                 185                 190

Leu Tyr Lys Asp Asp Phe Val Gly Ala Leu Ile Phe Ser Gly Ala
        195                 200                 205
```

(2) INFORMATION FOR SEQ ID NO:22:

(i) SEQUENCE CHARACTERISTICS:
        (A) LENGTH: 140 amino acids
        (B) TYPE: amino acid
        (C) STRANDEDNESS: unknown
        (D) TOPOLOGY: unknown (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: C. botulinum (xi) SEQUENCE DESCRIPTION: SEQ ID NO:22:

```
Leu Asn Ser Ser Leu Tyr Arg Gly Thr Lys Phe Ile Ile Lys Lys Tyr
1               5                   10                  15

Ala Ser Gly Asn Lys Asp Asn Ile Val Arg Asn Asn Asp Arg Val Tyr
                20                  25                  30

Ile Asn Val Val Val Lys Asn Lys Glu Tyr Arg Leu Ala Thr Asn Ala
            35                  40                  45

Ser Gln Ala Gly Val Glu Lys Ile Leu Ser Ala Leu Glu Ile Pro Asp
        50                  55                  60

Val Gly Asn Leu Ser Gln Val Val Met Lys Ser Lys Asn Asp Gln
65                  70                  75                  80

Gly Ile Thr Asn Lys Cys Lys Met Asn Leu Gln Asp Asn Asn Gly Asn
                85                  90                  95

Asp Ile Gly Phe Ile Gly Phe His Gln Phe Asn Asn Ile Ala Lys Leu
                100                 105                 110

Val Ala Ser Asn Trp Tyr Asn Arg Gln Ile Glu Arg Ser Ser Arg Thr
            115                 120                 125

Leu Gly Cys Ser Trp Glu Phe Ile Pro Val Asp Asp
        130                 135                 140
```

PROTECTIVE PEPTIDES NEUROTOXIN OF C. BOTULINUM

FIELD OF THE INVENTION

This invention relates to immunization against toxic effect of neurotoxins of *Clostridium botulinum*. Protective epitopes of the heavy chain of the neurotoxin of *C. botulinum* have been discovered. The invention also relates to preparation of protective immunotoxins of *C. botulinum*.

BACKGROUND OF THE INVENTION

Botulinum neurotoxin (BoNT) is one of the most potent toxins known to man. Ingestion or inhalation of toxin inhibits neurotransmitter release from synaptic vesicles, resulting in neuroparalysis and death. Seven serologically distinct forms of neurotoxin are produced by *Clostridium botulinum*. The toxin is synthesized as a 150 kDa precursor that is proteolytically nicked into two subunits. The light (L) chain, associated with the toxicity of BoNT, must be internalized in the cell in order to inhibit neurotransmitter release. It is linked by a disulfide bond to the heavy (H) chain, which mediates binding of the toxin to receptors located on the surface of the nerve cell. Although the heavy chain is required for BoNT to productively bind and enter the target cell, it is not toxic by itself.

The current pentavalent toxoid vaccine for botulism is composed of formalin-inactivated holotoxin. Although effective, this vaccine is difficult to manufacture. Furthermore, extensive treatment with formalin is required to inactivate the toxin. Prolonged treatment with formalin can affect the immunogenicity of protein antigens, and this may explain why certain lots of toxoid have been poorly immunogenic in the past.

There are several approaches that can be used to construct a new vaccine. One approach would be to express a nontoxigenic mutant of BoNT/A, as has already been done for other toxins. The advantage of this approach is that the immune response elicited by the modified protein would most closely approximate the response elicited by the native toxin, because almost all of the native protein structure would still be intact. However, high level expression of the C fragment of tetanus toxin (TeTx) could not be achieved in *E. coli* when the native clostridial gene sequence was used. Based on this information, expression of BoNT might be predicted to be difficult, as well. Another approach is to construct a synthetic peptide-based vaccine. The advantage of this approach is that large quantities of synthetic peptide can be easily manufactured for use in a vaccine. However, studies with MAbs have indicated that many of the neutralizing epitopes located on BoNT are conformationally sensitive. This suggests that a peptide-based vaccine may not necessarily be able to induce neutralizing antibody responses due to its lack of conformational epitopes. A genetically engineered vaccine for botulism would eliminate many problems, since it could be expressed in a recombinant host at high levels and would not require treatment with formalin before incorporation into a vaccine.

Recent developments have made the construction of a genetically engineered BoNT vaccine possible. The gene for BoNT serotype A (BoNT/A) has been cloned and sequenced (Binz, et al., *J. Biol. Chem.* 265:9153–9158.(1990), and the minimum length of the light chain needed to retain neurotoxicity has been defined (Kurazono, et al., *J. Biol. Chem.* 267:14721–14729 (1992)). While construction of such a vaccine is feasible, there has not been a systematic attempt to identify the domain(s) of BoNT/A that would be required to elicit protective immunity. Immunization with a fragment corresponding to the C-terminal half of the heavy chain ($H_C$) has been shown to stimulate protective immunity, but more definitive identification of sequences that elicit protective immune response had not previously been described. Monoclonal antibodies directed against either light chain or heavy chain determinants had been shown to provide some passive protection to mice against a lethal exposure to BoNT, indicating that protective epitopes may exist on either chain. However, many of these epitopes appear to be conformationally sensitive, which suggests that mapping their location by using synthetic peptides may be unproductive due to their lack of tertiary structure.

SUMMARY OF THE INVENTION

It is the purposes of this invention to provide methods for developing vaccines to protect from neurotoxins of *C. botulinum*. The methods used to identify specific sequences consisted of amplifying and cloning overlapping segments of the BoNT/A gene. These segments are then expressed in suitable vectors such as *E. coli* to produce truncated BoNT/A proteins of about 15–30 kDa in size. The truncated proteins are purified by appropriate methods such as SDS-PAGE. The invention is exemplified using two particularly protective regions from the heavy chain of the type A *C. botulinum* toxin. The peptides giving rise to protective antibodies may be fused to other peptides that act as adjuvants to increase antigenicity. Such fusion proteins may be produced by recombinant technology using plasmids containing hybrid genes for expression of the desired fusion proteins.

DETAILED DESCRIPTION OF THE INVENTION

It is the purpose of this invention to identify and provide immunogenic polypeptides which give rise to protective antibodies against botulism. Compositions containing the subject polypeptides in pharmaceutically acceptable carriers are useful as vaccines and as diagnostic agents to identify protective antibodies.

The location of protective domains was identified, and those domains were produced by expressing fragments of BoNT/A in *E. coli* and then evaluating each for its protective efficacy. Using this approach, fragments of the BoNT/A gene were expressed that were of sufficient size to still possess some tertiary conformation, but that would greatly reduce the amount of the toxin utilized. By overlapping the regions of the BoNT/A protein being expressed, it was possible to minimize the possibility that a locally encoded epitope was accidently interrupted. The advantage of this approach is that the fragments were sufficiently small to be nontoxic. However, it is possible that not all protective determinants may have been encoded by these fragments.

It was possible to express fragments of the BoNT/A gene at high levels in *E. coli* by using an inducible T7 expression system. It was not predictable that, in contrast to some of the problems encountered with expression of the C fragment of tetanus toxin (TeTx), this could be done for purposes of making a protective vaccine against botulism. Some difficulty encountered which was related to the fact that clostridial toxin is encoded by codons that are rarely used by *E. coli*. Unexpectedly, this problem with the DNA sequence naturally encoded by Clostridium did not present the barrier that might have been expected. The possibility for expression of these proteins may be due to the size of the BoNT/A proteins encoded. The TeTx proteins being expressed in *E. coli* were two to three times larger than the BoNT/A proteins expressed as disclosed herein. The smaller size of the BoNT/A transcripts may have permitted *E. coli* to translate them more efficiently. However, the truncated BoNT/A proteins were expressed primarily in the form of insoluble inclusion bodies. Insertion of the BoNT/A gene fragments into the plasmid vector pMTD74 resulted in expression of a BoNT/A protein fused to the A2 peptide of cholera toxin (CtxA2) at its C-terminus. These fragments were fused to CtxA2 to associate noncovalently with the B subunit of cholera toxin (CtxB). Fusion of antigens to CtxB was shown to improve their immunogenicity when administered by mucosal routes of immunization (Dertzbaugh, et al., *Infect. Immun.* 61:48–55 (1993)). Hence, CtxB is used as a delivery system with these fragments of BoNT/A as part of a mucosally administered vaccine for botulism.

The ability of the BoNT/A fragments to induce an antibody response was affected by the antigen preparation used for immunization. Effective production of antibody to BoNT/A was inadequate when the crude lysates were used for immunization, even though they contained relatively large amounts of BoNT/A-specific protein. For this reason, immunization was performed again with highly enriched preparations of the BoNT/A proteins. Unlike the crude form of the antigen, the purified form was able to elicit BoNT/A-specific antibody whilst being well tolerated by the animals. The poor immunogenicity of the crude lysates may have been due to saturation of the antigen-presenting cells with other antigens present. It is possible that by purifying the BoNT/A proteins, other immunodominant antigens were removed which could have been competing for uptake and presentation to lymphocytes by the antigen-presenting cells.

Preparative SDS-PAGE was used to purify the BoNT/A fragments for several reasons. First, most of the BoNT/A protein present in the lysates were in the form of inclusion bodies that had to be solubilized before purification. SDS easily solubilized the BoNT/A proteins. Second, this method can be used to purify all of the fragments, regardless of their size or composition. Furthermore, the size range of the BoNT/A proteins permitted them to be separated from most of the other proteins present in the lysates. One potential disadvantage of using such a denaturing method is that the purified BoNT/A proteins may not have completely resumed their native conformation, resulting in the loss of some epitopes. The BoNT/A proteins should have been able to refold when the SDS was removed from the antigen preparations before immunization.

Hybrid gene fusion proteins may also be produced to increase protective immune response. For example, DNA sequences which encode desired antigenic polypeptides may be fused to DNA sequences which encode non-toxic peptides of other organisms such as cholera. U.S. Pat. No. 5,268,276 to Holmgren, et al., which is incorporated herein in its entirety by reference, discloses a means of producing an appropriate fusion gene to produce fusion proteins containing the immunogenic peptides of botulism.

Both BoNT peptides and fusion proteins containing BoNT amino acid sequences may be administered by mouth. Antigenic fusion proteins containing sequences of cholera subunits are useful for administration orally or to the mucosa (for example intranasally). The fusion proteins may be lyophilized and inhaled from a vial for administration.

Compositions containing the BoNT peptides in pharmaceutically acceptable carriers may also be administered parenterally. Preferred parenteral routes include intracutaneous or subcutaneous or intramuscular injection. Any of the compositions may contain, additionally, adjuvants such as alum or Freund's adjuvant. While the invention has been exemplified using the peptides of *C. botulinum*, serotype A, analogous polypeptides sequences of other serotypes can be made in the manner described herein. A cocktail of polypeptides from various serotypes may be administered to provide broad protection against toxins of *C. botulinum* serotypes.

MATERIALS AND METHODS

Construction of the BoNT/A gene fragments. The polymerase chain reaction (PCR) was used to amplify and clone overlapping fragments of the BoNT/A gene. Primers used to amplify each fragment are listed in Table 1. The primers were designed to include unique flanking restriction sites on the 5' and 3' ends of each amplified fragment in order to permit its insertion into the expression vector. Plasmids pCBA2, pCBA3, and pCBA4 encoding large overlapping regions of the BoNT/A gene and flanking DNA were used as template DNA (Thompson, et al., *Eur. J. Biochem.* 73–81 (1990)). Amplification was performed using Vent DNA polymerase (New England Biolabs, Beverly, Mass.). The reaction mixture was prepared according to the manufacturer's directions, and consisted of 100 ng/µl forward primer, 100 ng/µl reverse primer, and 10 ng/µl template. Each reaction was subjected to 25 cycles of amplification in a DNA thermocycler according to the following parameters: melting temperature, 94° C. for 1 min; annealing temperature, 45° C. for 1 min; extension temperature, 72° C. for 1 min. The amplified DNA was digested with the appropriate restriction enzymes and then was ligated into the expression vector pMTD74.

TABLE 1

PCR primers

| n.t.[a] | Direction[c] | Sequence | |
|---|---|---|---|
| 367–741 | F: | 5'-ATATGGAATTCGTTAATAAACAATTTAATTATAAAGATCC-3' | Seq. #1 |
| $L_{4-128}$[b] | R: | 5'-AGTATCGTCGACTTTTAATTCTGTATCTATTGTACTTCCACC-3' | Seq. #2 |
| 732–1170 | F: | 5'-GATACAGAATTCAAAGTTATTGATACTAATAG-3' | Seq. #3 |
| $L_{126-271}$[b] | R: | 5'-CTTTGCGTCGACTCCCCCAAATGTTCTAAGTTCC-3' | Seq. #4 |
| 1126–1750 | F: | 5'-GGGTTAGAATTCAGCTTTGAGGAACTTAGAACATTTGGG-3' | Seq. #5 |
| $L_{257-465}$[b] | R: | 5'-AGGACTGTCGACCAAGTCCCAATTATTAACTTTGATTGATAAATC3' | Seq. #6 |
| 720–2340 | F: | 5'-TTAAATGAATTCTCAATCAAAGTTAATAATTGGGAC-3' | Seq. #7 |
| $H_{455-661}$[b] | R: | 5'-CTCTGGGTCGACTTCTAACAGAATAACAGCTCC-3' | Seq. #8 |
| 2150–2780 | F: | 5'-GAAGTAAGAGCTCTGGATAAAATTGCGGATATAAC-3' | Seq. #9 |
| $H_{630-808}$[b] | R: | 5'-TAACCGGTCGACACCATAAGGGATCATAGAG-3' | Seq. #11 |
| 2695–3175 | F: | 5'-GCTATGATTAATATAAATAAATTTTTGAATCAATGC-3' | Seq. #10 |
| $H_{780-939}$[b] | R: | 5'-AGTACTAAGCTTTTCATACATACTATTATATACAATAGC-3' | Seq. #12 |

TABLE 1-continued

PCR primers

| n.t.[a] | Direction[c] | Sequence | |
|---|---|---|---|
| 3100–3530 | F: | 5'-AAAAATAGAGCTCAATTATTTAATTTAGAAAGTAG-3' | Seq. #13 |
| $H_{915-1059}$[b] | R: | 5'-ACCATCGTCGACAAACATTATATTATTACTAGC-3' | Seq. #14 |
| 3301–3726 | F: | 5'-TATGGTGAATTCATCTGGACTTTACAGGATACTCAGG-3' | Seq. #15 |
| $H_{982-1123}$[b] | R: | 5'-ATTTACGTCGACATATTTATTTGGATC-3' | Seq. #16 |
| 3590–4020 | F: | 5'-GATAAGGAATTCAATGAAAAAGAAATCAAAG-3' | Seq. #17 |
| $H_{1078-1220}$[b] | R: | 5'-CTTCATGTCGACTACTTGACTTAGATTTCC-3' | Seq. #18 |
| 3806–4223 | F: | 5'-AACATTGAATTCAATTCAAGTTTGTATAGGGGG-3' | Seq. #19 |
| $H_{1150-1289}$[b] | R: | 5'-TCCATCGTCGACAGGAATAAATTCCCATGAGCTACC-3' | Seq. #20 |

[a]Nucleotide sequence number designation based on EMBL/Genbank ™ accession file X52066.
[b]Amino acid residue number of the light (L) chain and the heavy (H) chain.
[c]F, forward primer; R, reverse primer.

Bacterial strains and plasmids. Plasmids constructed are listed in Table 2. All plasmids were transformed by the $CaCl_2$-heat shock method (See Morrison, D. A., *J. Bacteriol.* 132:349–351 (1977)) into *E. coli* strain HMS174(DE3) (Campell, et al., *Proc. Natl. Acad. Sci., U.S.A.,* 75:2276–2280 (1978)). Bacterial strains were grown at 37° C. in M-9 medium in accord with the methods of Miller (Miller, J. H., *Experiments in Molecular Genetics,* Cold Spring Harbor Laboratory, Cold Spring Harbor (1972)) supplemented with 10 g of Casamino Acids (Difco Laboratories, Ann Arbor, Mich.) per liter, 20 μg of leucine per ml, 20 μg of proline per ml, 2 μg of thiamine per ml, 50 μg of ampicillin per ml, and 25 μg of rifampicin per ml. Plasmid pMTD74 was used to express the BoNT/A fragments in *E. coli*. It was derived from the T7 translation vector pET-8c (Studier, et al., *Methods in enzymology,* Academic Press, New York (1990)) and has a multiple cloning site encoding unique restriction sites. This plasmid was used to express fragments of the BoNT/A gene in *E. coli* . It encodes a gene for ampicillin (Ap) resistance and a ColE1 origin of replication (ORI). Transcription is initiated from the T7 promoter and is terminated by the Tϕ transcriptional terminator (t.t.). Proper in-frame insertion of DNA within the multiple cloning site (MCS) results in expression of protein fused to the A2 peptide of cholera toxin (CtxA2). (Lockman, et al., *J. Biol. Chem.* 258:13722–13726 (1983)). The MCS contains several unique restriction sites, and is shown in more detail below the plasmid map. Translation is initiated by the Shine-Delgarno (S.D.) sequence located upstream of the initiator methionine encoded by the NcoI site. Transformation of this plasmid into the lysogenic *E. coli* strain HMS174(DE3) permits inducible expression of protein from the T7 promoter. T7 RNA polymerase is required for initiation of transcription from the T7 promoter, and this protein is inducibly expressed in HMS174(DE3) by using isopropyl-beta-D-thiogalactopyranoside (IPTG).

TABLE 2

Bacterial strains and plasmids

| *E. Coli* Strain | Plasmid | Comments | References |
|---|---|---|---|
| | pMTD74 | | |
| HMS174 | | $F^-$ hsdR($r_K^-$ $m_K^+$) recA $rif^R$ | Campbell* |
| HMS174(DE3) | | T7 expression host | Studier** |
| MTD103 | pMTD89 | BoNT/A $L_{4-128}$ | |
| MTD143 | pMTD143 | BoNT/A $H_{455-661}$ | |
| MTD145 | pMTD130 | BoNT/A $H_{780-939}$ | |

TABLE 2-continued

Bacterial strains and plasmids

| *E. Coli* Strain | Plasmid | Comments | References |
|---|---|---|---|
| MTD150 | pMTD74 | HMS174(DE3) host for background control | |
| MTD164 | pMTD162 | BoNT/A $H_{982-1123}$ | |
| MTD165 | pMTD163 | BoNT/A $H_{1150-1289}$ | |
| MTD191 | pMTD186 | BoNT/A $L_{126-271}$ | |
| MTD193 | PMTD188 | BoNT/A $H_{1078-1220}$ | |
| MTD196 | pMTD187 | BoNT/A $L_{257-465}$ | |
| MTD203 | PMTD195 | BoNT/A $H_{915-1059}$ | |
| MTD210 | pMTD148 | BoNT/A $H_{630-808}$ | |

*Campbell, et al., Proc.Natl.Acad.Sci.,U.S.A. 75:2276–2280 (1994)
**Studier, et al., MethodsinEnzymology, Academic Press, New York (1990)

Analysis of protein expression. Transformants were screened for protein expression by immunoblotting analysis. Individual colonies were grown at 37° C. in 2 ml of M-9 medium to an optical density of 0.8–1.0 at 660 nm. Expression was induced by adding IPTG to a concentration of 0.25 mM. After induction, cultures were incubated at 37° C. for 2 h before harvesting. The cells were pelleted in a microfuge tube and resuspended in 100 μl of sample loading buffer containing 1% sodium dodecyl sulfate (SDS) and 0.2 M 2-mercaptoethanol. The samples were boiled for 5 min and then separated by discontinuous SDS-polyacrylamide gel electrophoresis (PAGE) (Lammeli, U. K., Nature 227:680–685 (1970)). The proteins were transferred to nitrocellulose sheets using a semi-dry electroblotter (Integrated Separation Systems, Hyde Park, Mass.) and then stained for the presence of BoNT/A-specific protein using horse antiserum to BoNT/A. Strain MTD150 was prepared as described above and used as a background control. Purified BoNT/A (Sigma, St. Louis, Mo.) was included in each gel as a positive control.

Cell fractionation. Bacterial strains encoding the truncated BoNT/A proteins were grown in M-9 medium and were induced to express protein as described above. Cells were pelleted by centrifugation at 3,000×g for 10 min. The pellet was suspended in lysis buffer containing 1 mg/ml lysozyme, 50 mM Tris, 50 mM EDTA, and 20% sucrose (pH 8.0) and was incubated at 37° C. for 30 min. To ensure complete lysis, the cell suspension was subjected to two cycles of rapid freeze-thaw. $MgSO_4$ was added to the lysate to a concentration of 20 mM, DNase (Sigma) and RNase (Sigma) were added to a concentration of 0.01 mg/ml each, and then the lysate was incubated at 37° C. for 30 min. The lysate was clarified by centrifugation at 3,000×g for 10 min. The clarified lysate was centrifuged at 20,000×g for 30 min at 4° C. and the resulting pellet was dissolved in sample loading buffer. The sample was boiled for 5 min and stored at −20° C. before use.

Purification of BoNT/A proteins. The truncated BoNT/A proteins were purified by preparative SDS-PAGE with a Model 491 Prep Cell (Bio-Rad, Richmond, Calif.). The percentage of acrylamide used in the resolving gel was adjusted to maximize the separation of the protein of interest. Separation was typically performed at 12 watts constant power with a 37-mm diameter tube gel. The length of the stacking and resolving gels were 2 cm and 10 cm, respectively. The eluate was collected at a flow rate of 0.75 ml/min as 4-ml fractions. Aliquots of the fractions were separated by analytical SDS-PAGE and stained with Coomassie blue to visualize total protein. In some cases, a duplicate gel was transferred to nitrocellulose and analyzed for immunoreactivity to polyclonal horse antiserum to BoNT/A. Fractions containing truncated BoNT/A protein were pooled and concentrated by ultrafiltration (Amicon, Danvers, Mass.). The concentrated protein was passed through a column containing Extracti-Gel™ D resin (Pierce, Rockford, Ill.) to remove any remaining SDS. The protein was subjected to extensive diafiltration in buffer containing 120 mM NaCl, 2.7 mM KCl, 10 mM phosphate buffer (pH 7.4), 20% glycerol (v/v), and 5 mM EDTA. Each protein preparation was examined by Coomassie staining and immunoblotting analysis for its composition and for the presence of BoNT/A-specific protein . Protein concentrations were determined by the BCA assay (Pierce). The protein preparations were aliquoted and stored at −70° C. before use.

Immunization and challenge. The protocol used in this study was approved by the USAMRIID Institutional Animal Care and Use Committee. Female CB6F1 mice (Jackson Laboratory, Bar Harbor, Me.), 4–6 weeks old, were provided food and water ad libitum. The mice were immunized with 10 µg of BoNT/A-specific protein suspended in adjuvant emulsion (Ribi Immunochem, Hamilton, Mont.). some mice were immunized with saline emulsified in adjuvant for use as negative controls. For comparison, some mice were immunized with pentavalent toxoid. The mice were immunized i.p. four times at 2-week intervals. One week after the last immunization, the mice were bled and the serum was analyzed by immunoblot for the presence of chain-specific antibody. Two weeks after the last immunization, each mouse was challenged i.p. with 2 lethal doses of BoNT/A (2 MIPLD$_{99}$). Four days after challenge, the mice were scored for survivors.

Immunoblotting analysis. BoNT/A was separated by SDS-PAGE on a 10% gel and then transferred to nitrocellulose using a semi-dry electroblotter. The nitrocellulose was blocked and loaded into a Multi-Screen immunoblotting apparatus (Bio-Rad). Pooled serum from each group of immunized mice was diluted and then incubated in separate wells of the apparatus. The blot was developed using an alkaline phosphatase-conjugated goat antibody to mouse IgG (Kirkegaard & Perry Labs, Gaithersburg, Md.) to identify the presence of BoNT/A-specific antibody.

Construction and expression of BoNT/A gene fragments. The BoNT/A gene was subcloned into overlapping fragments ranging in size from ~300–600 base pairs by using PCR. The primers encoded flanking restriction sites that permitted convenient insertion into the expression vector used, and allowed transcriptional and translational read-through of the amplified fragments to occur (Table 1). Plasmid vector pMTD74 was used to express the amplified BoNT/A gene fragments in *E. coli* . Insertion of the PCR-amplified fragments into the expression vector pMTD74 resulted in translational fusion to the A2 peptide of cholera toxin (CtxA2) (8). The fragments were fused to CtxA2 to provide a vaccine for administration mucosally. The presence of BoNT/A-specific protein was determined by immunoblotting analysis, using polyclonal horse antiserum to BoNT/A, and by comparison of the predicted size of the truncated protein to its actual size. Fusion to CtxA2 increased the predicted size of the truncated BoNT/A proteins expressed by an additional 5.4 kDa, but it did not appear to affect their ability to be produced. By expressing overlapping segments of the toxin, all potential linear epitopes were encoded. BoNT/A is post translationally cleaved into the light (L) and heavy (H) chains which are joined together by a disulfide bond. The position of each fragment within BoNT/A is indicated by the chain it was derived from (L or H), followed by the amino acid residues of BoNT/A encoded.). The T7 promoter expressed these proteins at high levels in *E. coli* . The BoNT/A-specific proteins were expressed primarily in the form of inclusion bodies that could be isolated by differential centrifugation upon lysis of the cells.

Purification of BoNT/A proteins. While the crude lysates containing the BoNT/A proteins were initially used for immunization of mice, it was found preferable to use at least partially purified materials to provide improved tolerance and to effectively produce strong, specific antibody response. For these reasons, the lysates containing the truncated BoNT/A proteins were subjected to purification by preparative SDS-PAGE and then used for immunization of mice. Preparative SDS-PAGE provided a convenient method of both solubilizing and separating the BoNT/A proteins from the majority of other contaminants present in the lysates. Although the BoNT/A proteins were not always purified to homogeneity, they were highly enriched. Furthermore, the BoNT/A proteins remained soluble after the SDS was removed, which facilitated the administration of these proteins to mice.

Immunogenicity of BoNT/A proteins. Mice were immunized i.p. with the truncated BoNT/A proteins emulsified in Ribi™ adjuvant. The mice were immunized at 2-week intervals, and one week after the last immunization, their serum was analyzed for the presence of antibody to BoNT/A. Since BoNT/A can be separated by SDS-PAGE into a 50 kDa light chain and 100 kDa heavy chain, immunoblotting analysis was used to evaluate whether the antibody elicited by each truncated protein reacted with the appropriate chain. Optimal antibody responses were observed in mice after the fourth dose. All of the truncated proteins were able to elicit an antibody response except $H_{1078-1220}$. Although this fragment was non-immunogenic, it was highly antigenic when reacted with polyclonal horse antiserum to BoNT/A. Unlike the crude lysates used for immunization previously, the purified proteins were well-tolerated and could be repeatedly administered to the mice. In addition, the purified proteins were able to elicit an BoNT/A-specific antibody response in mice. This difference in the immunogenicity of the crude lysates cannot be accounted for by the lack of BoNT/A-specific protein, since the lysates used for immunization were known to contain appreciable quantities of truncated protein.

Protective efficacy of BoNT/A proteins. Two weeks after the final immunization, each mouse was challenged i.p. with 2 lethal doses of BoNT/A (2 MIPLD$_{99}$). This dose was chosen for initial screening to observe any potential ability of the proteins to elicit protective immunity. As shown in Table 3, only two proteins protected the majority of animals from death. Both of these fragments were derived from the heavy chain and encoded amino acid residues $H_{455-661}$ and $H_{1150-1289}$.

$H_{455-661}$ of serotype A neurotoxin is the sequence

H$_3$N-IKVNN WDLFF SPSED NFTND LNKGE EITSD TNIEA AEENI SLDLI QQYYL TFNFD NEPEN ISIEN LSSDI IGQLE LMPNI ERFPN GKKYE LDKYT MFHYL RAQEF EHGKS RIALT NSVNE ALLNP SRVYT FFSSD YVKKV NKATE AAMFL GWVEQ LVYDF TDETS EVSTT DKIAD ITIII PYIGP ALNIG NMLYK DDFVG ALIFS GA-COOH Seq. #21 and $H_{1150-1289}$ of serotype A neurotoxin is the sequence

H$_3$N-LNSSL YRGTK FIIKK YASGN KDNIV RNNDR VYINV VVKNK EYRLA TNASQ AGVEK ILSAL EIPDV GNLSQ VVVMK SKNDQ GITNK CKMNL QDNNG NDIGF IGFHQ FNNIA KLVAS NWYNR QIERS SRTLG CSWEF IPVDD-COOH Seq. #22.

Although some of the other truncated proteins appeared to provide partial protection at the challenge dose initially used, none were as definitive as $H_{455-661}$ and $H_{1150-1289}$. Rechallenge of the survivors with 2 MIPLD$_{99}$ of BoNT/A resulted in the death of all mice except those immunized with the two protective fragments. To confirm these results, separate groups of mice were immunized with fragments $H_{455-661}$ and $H_{1150-1289}$ as before and then challenged with 10 MIPLD$_{50}$. The survival rate for mice immunized with $H_{455-661}$ and $H_{1150-1289}$ at this challenge dose was determined to be 87.5% and 60.0%, respectively.

TABLE 3

Immunogenicity and protective efficacy of the truncated BoNT/A proteins

| Protein Segment[a] | Immuno-Blot[b] | Number of Survivors[c] | % Survival |
|---|---|---|---|
| L$_{4-128}$ | + | 1/10 | 10.0 |
| L$_{126-271}$ | + | 0/8 | 0.0 |
| L$_{257-465}$ | + | 0/9 | 0.0 |
| H$_{455-661}$ | + | 7/9 | 77.8 |
| H$_{630-808}$ | + | 0/5 | 0.0 |
| H$_{780-939}$ | + | 2/7 | 28.6 |
| H$_{915-1059}$ | + | 0/8 | 0.0 |
| H$_{982-1123}$ | + | 1/9 | 11.1 |
| H$_{1078-1220}$ | − | 0/5 | 0.0 |
| H$_{1150-1289}$ | + | 6/8 | 75.0 |

[a]Amino acid residue number of the light (L) chain and the heavy (H) chain.
[b]CB6F1 mice were immunized i.p. with four doses of each protein at 2-week intervals. One week after the last dose, the mice were bled and the serum was analyzed by immunoblot for the presence of antibody specific for BoNT/A.
[c]Number of survivors/total number 4 days after challenge with 2 MIPLD$_{99}$ of BoNT/A.

Immunoblotting analysis was used to detect the presence of BoNT/A-specific antibody in the immunized mice for several reasons. First, the sensitivity of this method maximized the probability of detecting the presence of any fragment-specific antibody, regardless of whether it was directed towards a linear or a conformational epitope. Second, by separating BoNT/A into its heavy and light chains, this procedure also permitted the chain specificity of the antibody to be confirmed. By this method, all fragments were able to elicit an antibody response, except $H_{1078-1220}$.

Although most of the BoNT/A fragments were able to elicit antibody, only two were clearly able to confer protective immunity (Table 3). The protective efficacy of $H_{455-661}$ and $H_{1150-1289}$ correlates well with the potential functional role of these domains. The N-terminal half of the heavy chain (H$_N$) of BoNT/A, from which $H_{455-661}$ was derived, has been shown to be important in productive binding and internalization of the toxin to the cell. The C-terminal half of the heavy chain (H$_C$), from which $H_{1150-1289}$ was derived, has been associated with the initial binding of the toxin to the cell. If these functions are encoded by either fragment, then antibody specific to these domains would be predicted to interfere with the binding and/or internalization of BoNT/A. This, in turn, would prevent intoxication of the cell. The location of these protective domains on the extreme N- and C-terminal ends of the heavy chain suggest that important functional roles may also be encoded by these fragments. We are currently exploring this possibility.

The light chain fragment $L_{126-271}$, did not confer protection even though it elicited an antibody response (Table 3). This fragment encodes a highly conserved histidine-rich motif characteristic of zinc-dependent metalloproteases, such as BoNT/A. Although unproven, antibody directed to this region may block the enzymatic activity of BoNT/A. The inability of $L_{126-271}$ to protect suggests that the antibody elicited by this fragment may not have been directed towards epitopes involved in the enzymatic activity of the light chain.

Studies with MAbs suggest that many of the antibody determinants of BoNT/A may be conformationally sensitive, and there is evidence to suggest that BoNT/A is an oligomeric protein. If BoNT/A is indeed oligomeric, then it is possible that some epitopes are formed by the interaction of adjoining subunits. Alternatively, linear-distant parts of the toxin molecule may come together when folded to form epitopes, as appears to be the case for the light chain. Comparison of the amino acid sequence of these fragments with the amino acid sequence of similar regions from the other serotypes did not show any significant homology. A cocktail of recombinant proteins containing amino acid sequences from analogous domains other serotypes (H$_{455-661}$ and H$_{1150-1289}$) should be prepared using the methods of the invention to provide immune protection against more than one serotype of organism.

The entire domains of $H_{455-661}$ and/or $H_{1150-1289}$ need not be used to provide a vaccine. However, at least 100 amino acids from one of the domains of any serotype should be used to provide sufficient antigenicity and immunoprotection.

What is claimed is:

1. An isolated polypeptide consisting of at least 100 amino acids from either sequence H$_3$H-IKVNN WDLFF SPSED NFTND LNKGE EITSD TNIEA AEENI SLDLI QQYYL TFNFD NEPEN ISIEN LSSDI IGQLE LMPNI ERFPN GKKYE LDKYT MFHYL RAQEF EHGKS RIALT NSVNE ALLNP SRVYT FFSSD YVKKV NKATE AAMFL GWVEQ LVYDF TDETS EVSTT DKIAD ITIII PYIGP ALNIG NMLYK DDFVG ALIFS GA-COOH (Seq. ID No. 21)

or

H$_3$N-LNSSL YRGTK FIIKK YASGN KDNIV RNNDR VYINV VVKNK EYRLA TNASQ AGVEK ILSAL EIPDV GNLSQ VVVMK SKNDQ GITNK CKMNL QDNNG NDIGF IGFHQ FNNIA KLVAS NWYNR QIERS SRTLG CSWEF IPVDD-COOH (Seq. ID NO. 22).

2. A composition of matter comprising at least one polypeptide of claim 1 in a carrier.

3. An isolated fusion protein of wherein a first polypeptide consisting of at least 100 amino acids is from either sequence H$_3$H-IKVNN WDLFF SPSED NFTND LNKGE EITSD TNIEA AEENI SLDLI QQYYL TFNFD NEPEN ISIEN LSSDI IGQLE LMPNI ERFPN GKKYE LDKYT MFHYL RAQEF EHGKS RIALT NSVNE ALLNP SRVYT FFSSD YVKKV NKATE AAMFL GWVEQ LVYDF TDETS EVSTT DKIAD ITIII PYIGP ALNIG NMLYK DDFVG ALIFS GA-COOH (Seq. ID NO. 21)

or

H$_3$N-LNSSL YRGTK FIIKK YASGN KDNIV RNNDR VYINV VVKNK EYRLA TNASQ AGVEK ILSAL EIPDV GNLSQ VVVMK SKNDQ GITNK CKMNL QDNNG NDIGF IGFHQ FNNIA KLVAS NWYNR QIERS SRTLG CSWEF IPVDD-COOH (Seq. ID NO. 22) is fused to a second polypeptide which acts as an adjuvant.

4. A polypeptide of claim 3 wherein the second polypeptide is 2A polypeptide of cholera toxin.

5. A method of immunizing a mammal susceptible to botulism by administration of a composition of claim 2.

* * * * *